United States Patent
Peter et al.

(10) Patent No.: US 7,862,544 B2
(45) Date of Patent: *Jan. 4, 2011

(54) DRIVE DEVICE FOR A PISTON IN A CONTAINER CONTAINING AN INJECTABLE PRODUCT

(75) Inventors: Daniel Peter, Niederwangen (CH); Beat Spoerri, Bibern (CH); Hanspeter Niklaus, Riken (CH)

(73) Assignee: Roche Diagnostics International AG, Steinhausen (CH)

( * ) Notice: Subject to any disclaimer, the term of this patent is extended or adjusted under 35 U.S.C. 154(b) by 454 days.

This patent is subject to a terminal disclaimer.

(21) Appl. No.: 11/755,439

(22) Filed: May 30, 2007

(65) Prior Publication Data

US 2008/0023492 A1    Jan. 31, 2008

Related U.S. Application Data

(63) Continuation of application No. 10/256,276, filed on Sep. 26, 2002, now Pat. No. 7,273,472, which is a continuation of application No. PCT/CH01/00155, filed on Mar. 13, 2001.

(30) Foreign Application Priority Data

Mar. 27, 2000   (DE) ............................... 100 15 175

(51) Int. Cl.
*A61M 37/00* (2006.01)
(52) U.S. Cl. ....................................... 604/155; 604/131
(58) Field of Classification Search .................. 604/19, 604/65, 151, 207, 211, 232, 155, 131
See application file for complete search history.

(56) References Cited

U.S. PATENT DOCUMENTS

| 4,950,246 A | 8/1990 | Muller |
| 4,973,318 A | 11/1990 | Holm et al. |
| 5,674,204 A | 10/1997 | Chanoch |
| 5,921,966 A | 7/1999 | Bendek et al. |
| 7,273,472 B2 | 9/2007 | Peter et al. |

FOREIGN PATENT DOCUMENTS

| WO | 9847552 | 10/1998 |
| WO | WO 9847552 A1 * | 10/1998 |

* cited by examiner

*Primary Examiner*—Nicholas D Lucchesi
*Assistant Examiner*—Brooke M Matney
(74) *Attorney, Agent, or Firm*—Dorsey & Whitney LLP

(57) ABSTRACT

A drive arrangement for an injection device, including a first stage, a second stage and a drive for shifting the stages, wherein the drive acts on one of the stages to shift said one of the stages first and wherein the stage which is first shifted encounters a higher resistance than does the other stage, such that the other stage is shifted.

18 Claims, 5 Drawing Sheets

Schnitt B-B

Schnitt C-C

DRIVE DEVICE FOR A PISTON IN A CONTAINER CONTAINING AN INJECTABLE PRODUCT

PRIORITY CLAIM

This application is a Continuation application of PCT/CH01/00155, filed on Mar. 13, 2001, which claims priority to German Patent Application No. DE 100 15 175.2, filed on Mar. 27, 2000, both of which are incorporated herein by reference.

BACKGROUND

The invention relates to a drive for a piston in a container containing an injectable product.

Portable injection and/or infusion devices are used to administer for example medicines in fluid form, in particular in liquid form, for example insulin. The medicine fluid is displaced from a fluid container by means of a piston and administered in precise doses.

Drive devices for the piston of the type which are preferred for the purposes of the present invention are known from WO 98/47552. These are telescopic drives, in which a first shifting stage shiftably mounted in or on a base part advances the piston in an advancing direction in the container when it is itself advanced, displacing the product from the container. In addition to the first shifting stage, at least a second shifting stage is provided which can be shifted in the advancing direction relative to the base part and which slaves the first shifting stage in the advancing direction when it is shifted. The shifting stages are shifted relative to the base part and to each other by spindle drives. By using a number of spindle drives, a long shifting path can be set precisely. However, thread pairings, such as those formed by spindle drives, exhibit axial play. The magnitude of the play is determined by the thread tolerances.

SUMMARY

A object of the invention is to improve the precision of dosing a medicinal product, using an injection device or an portable infusion device.

In one embodiment, the present invention involves injection devices and comprises a drive arrangement comprising a first stage, a second stage and a drive for shifting the stages, wherein the drive acts on one of the stages to shift said one of the stages first and wherein the stage which is first shifted encounters a higher resistance than does the other stage, such that the other stage is shifted.

The invention starts from the following recognition: after the product has been completely delivered from the container, the shifting stages are situated in a front position. From this front position, the shifting stages are shifted back to a starting position and are ready for new product to be administered. In the starting position, the shifting stages are each retracted against a fixed stopper or other suitable stop structure. Those thread flanks of the spindle drives which form the driving flanks during retraction are the driven flanks when the shifting stages are extended. The driving flanks of each of the spindle drives alternate between extending and retracting. Due to the thread play, the driving threads during extension each have to complete a certain rotational movement before a driving flank of the driving thread presses against a counter flank of the driven thread of the spindle drive and causes the driven shifting stage to advance. If a shifting stage is advanced from the starting position in the advancing direction, then a rotational movement of a driving thread only generates an advancing movement of said shifting stage when the play in the spindle drive has been compensated for, i.e., when at least one driving flank of the driving thread presses against a counter flank of the thread of the driven shifting stage.

The conditions described above apply in principle before each first extension following a complete or partial retraction. If a drive device comprises two or more shifting stages, and said two or more shifting stages are to be extended for the first time after having been retracted, then the shifting positions of said shifting stages are not defined within the context of the thread play.

In accordance with the present invention, the shifting stage of at least two shifting stages, which is advanced as the first of said two shifting stages from a starting position by a pre-set shifting path length, is prevented from advancing further, beyond the pre-set shifting path length. It experiences, at least in sections, a higher resistance against advancing further than does the other shifting stage, such that the other shifting stage is likewise advanced. The resistance cited is at least sufficiently large for the other shifting stage to be extended a first time, i.e., it is larger than the unavoidable resistance which has to be overcome in order to extend the other shifting stage. The increased resistance can, however, be overcome by the drive. The pre-set shifting path length is non-zero, but is preferably selected to be as small as possible. In any event, the shifting stage in question is advanced some way under the influence of the spindle drive driving it, since in this case the thread play has definitely been compensated for. The pre-set shifting path length is preferably selected to be smaller than the distance by which the piston has to be advanced when primed, despite the play having been compensated for, when the parts of the administering device which guide the product are to be vented. The play in the spindle drives is thus already compensated for as the device for administering the product is primed.

In one embodiment, the present invention comprises a drive arrangement for an injection device, the drive arrangement comprising a first shifting stage, a second shifting stage which, when shifted, slaves the first shifting stage, wherein the first shifting stage may be shifted relative to the second shifting stage and the first and second shifting stages at least partially overlap, and a drive for shifting the shifting stages, wherein the drive acts on one of the shifting stages via a first spindle drive and wherein a second spindle drive is formed between the shifting stages, and further wherein the shifting stage which is first shifted encounters a higher resistance than does the other shifting stage, such that the other shifting stage is shifted.

The shifting stage which extends as the first of the shifting stages from the starting position can be clearly determined in advance using constructive measures. For instance, the thread frictions of the two spindle drives can be selected differently, for example by selecting appropriate materials. Instead or in addition, the shifting stage which is not to be advanced as the first can persist in its starting position due to a slight pressing fit, as long as the shifting stage which is predetermined in this way as the first to be advanced has not yet experienced the increased resistance. As soon as the increased resistance has been established, the shifting stage is released from its pressing fit and is then advanced. In order to obtain resistances of different magnitudes against the first extension, the mesh lengths of the threads of the two spindle drives during full mesh or only in the starting position of the shifting stages can also be selected so as to be of different magnitudes. The shifting stage which is driven by the spindle drive with the shorter thread mesh, at least in the starting position, extends as the first shifting stage and experiences the higher resistance, at least in sections, once the pre-set path length has been covered.

The higher resistance, at least in sections, can be generated by forming an advancing brake acting between the shifting stage which advances as the first shifting stage and the other shifting stage or another body relative to which the shifting stage which advances first may be shifted in the advancing direction. The other body can be non-shiftably connected to the base part or formed by the base part itself.

In some preferred embodiments, a resistance area is formed on a surface area of the shifting stage which advances first, and a resistance counter area is formed on a surface area relative to which the shifting stage which advances first may be shifted in the advancing direction. The higher resistance, at least in sections, is generated by a pressure exerted by the resistance area onto the resistance counter area. The resistance area and the resistance counter area form a advancing brake, either on their own or in co-operation with a resistance element or a number of resistance elements.

The advancing brake can be based solely on sliding friction. An increased sliding friction in sections can be obtained by forming each of the resistance area and the resistance counter area as a narrow strip in the advancing direction. The roughness of the resistance area and the roughness of the resistance counter area are such that a resistance is generated when these two areas slide over one another, said resistance ensuring that the shifting stage which advances first is fixed and the at least one other shifting stage is advanced, but wherein said resistance can on the other hand be easily overcome by driving the drive device.

The resistance area and the resistance counter area are advantageously formed by a collar formed on each of the surface areas in question. The collars can each be formed by a radial protrusion or bulge. This protrusion or bulge can be flexible, such that the collar formed by it gives under a pressure exerted by the other collar, but still does not expose the path, in order to firstly generate the higher resistance in accordance with the invention. In some embodiments, the resistance area and the resistance counter area can both be flexible. In some embodiments, the radial protrusion or bulge is preferably formed to run or extend around the whole circumference. In sections, it reduces a radial distance formed between the shifting stage in question and the surface area facing it.

In one preferred embodiment, a resistance element is arranged between the resistance area and the resistance counter area, the resistance area exerting the pressure force onto the resistance counter area via said resistance element. If said resistance element is flexible, as in some preferred embodiments, the resistance area and the resistance counter area can be non-flexible. The resistance element gives under the pressure force, or suction force as the case may be, of the shifting stage which advances first. It offers resistance to said shifting stage advancing further, which preferably increases with the degree of flexing.

In some preferred embodiments, the resistance element is elastically flexible. It is formed as a spring element which exerts an axial force onto the shifting stage, counter to the advancing direction, when the shifting stage tenses the spring element. A spiral spring can, for example, be provided, which is integrated in the drive device perpendicular to the advancing direction of the shifting stage. The spiral spring exerts a resistance force onto the shifting stage, against the advancing direction, when it is ejected at its exposed end. The spiral spring can be held on the shifting stage or on a surface area facing it, relative to which the shifting stage can be shifted.

In some embodiments, the resistance against the shifting stage advancing is only increased in a partial region of the advancing path. Only one point on the shifting path of the shifting stage is needed at which the resistance of said shifting stage is increased relative to the other shifting stage. The shifting stage which experiences a higher resistance remains at this point until an even greater resistance opposes the other shifting stage. At the latest, this is the case when the other shifting stage has reached its maximum extending length. The shifting stage which is braked or stopped first is then moved beyond the region in which an increased resistance counteracts it, and subsequently moves onwards—preferably again under low resistance—as far as the point of maximum shifting, i.e., minimum overlap between the shifting stages.

In one preferred embodiment, the resistance element is formed by an O-ring, which may be made of plastic. A spring-elastic element, such as, for example, an annular spring made of metal or plastic, or an annular spiral spring, can also be used.

In one preferred embodiment, the resistance element is formed by an elastically flexible clip. The clip protrudes into the shifting path of the shifting stage which advances first and is ejected by the advancing shifting stage. The clip can instead also be attached to the shifting stage and push against a collar on the surface area facing it.

In some embodiments, an advancing brake is preferably provided for each of the shifting stages. Each of the number of advancing brakes may be formed like one of the embodiments described above.

In one preferred embodiment, a single flexible resistance element is used for the first and the second shifting stage. This common resistance element is preferably non-shiftably connected to one of the shifting stages or to the base part.

The at least two shifting stages can only be definitively extended without a separate advancing brake, using only the threads of the spindle drives. In this embodiment, the spindle drives are purposefully produced with different thread frictions per convolution, i.e., with different specific thread frictions. The shifting stage which advances first is driven by a spindle drive with the greater specific thread friction. However, the thread mesh of this spindle drive is shorter, in the starting position of the shifting stage which it drives, than the thread mesh of the other spindle drive in the starting position of the other shifting stage. The lengths of the two thread meshes in the starting position are selected such that smaller friction forces occur, despite the greater thread friction in the one spindle drive, due to the smaller thread mesh in the starting position. In this way, the shifting stage driven by this spindle drive is determined in advance as the shifting stage which advances first. As the thread mesh increases in length, however, the frictional resistance increases, until it exceeds the frictional resistance of the other spindle drive. At the latest, this state results when there is full thread mesh in the spindle drive with the greater specific thread friction. Special high-friction braking zones can also be provided in the threads at appropriate points.

DETAILED DESCRIPTION

Figure 1:
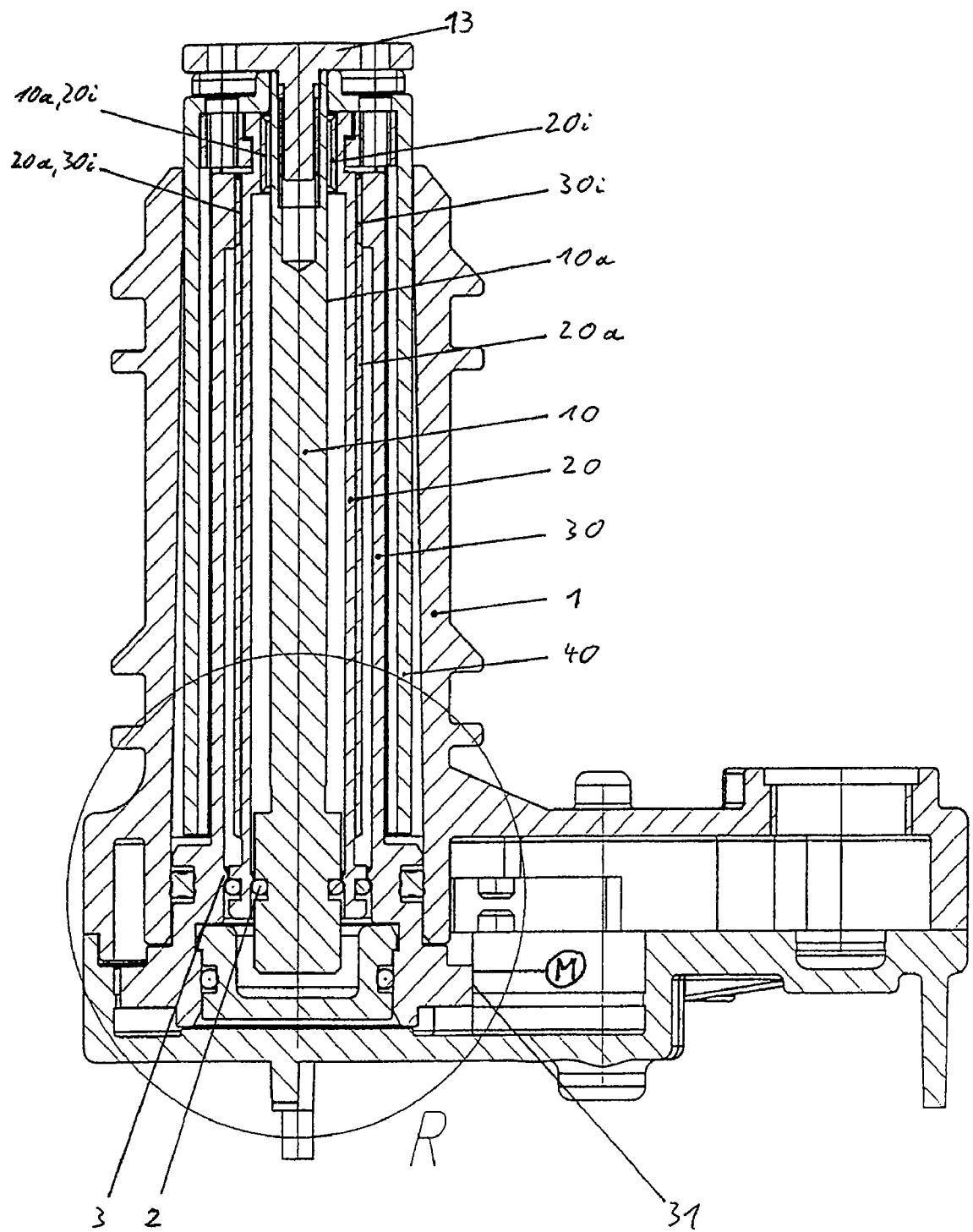
FIG. 1 depicts a drive device for a piston of an infusion device, in its starting position.

FIG. 1 shows a longitudinal section through a drive device. The drive device comprises as its main components: a base part 1; two shifting stages 10 and 20 which can be linearly shifted relative to the base part 1; and an axially fixed rotary drive member 30 which is rotary mounted in the base part 1 and forms the drive. The first shifting stage 10 is formed as a threaded rod comprising an external thread 10a. The second shifting stage 20 is a threaded sleeve comprising an internal thread 20i and an external thread 20a. The rotary drive member 30 is a hollow cylinder and will be referred to herein as the drive 30. The drive 30 comprises an internal thread 30i on a head region and a slaving toothing 31 on a foot region, by which the drive 30 is driven by a motor.

The threaded sleeve 20 and the drive 30 form a first spindle drive via their threads 20a and 30i. The threaded rod 10 and the threaded sleeve 20 form a second spindle drive via their threads 10a and 20i. The two sleeves 20 and 30 surround the threaded rod 10 concentrically with a common central longitudinal axis which simultaneously lies in the advancing direction of the drive device. The drive device shifts a piston, which is accommodated in a reservoir or container containing a medicine fluid, in this advancing direction when the shifting stages are advanced, in that the threaded rod 10—as the foremost or first shifting stage, pressing against the piston via a front plunger 13—advances said piston towards an outlet of the container and thus displaces liquid from the container. The base part 1 fixes the drive device relative to the container. The base part 1 can be attached to a casing accommodating the container or can be formed by a casing of an injection and/or infusion device. In such a casing, the base part is preferably mounted floating and may be linearly shifted in the advancing direction.

A rotational movement of the drive sleeve 30 is transmitted onto the threaded sleeve 20 via the first spindle drive formed between the threads 20a, 30i. Depending on the frictional forces acting on the threaded sleeve 20, the threaded sleeve 20 is either rotationally slaved or shifted along its rotational axis by the first spindle drive comprising the threads 20a, 30i. The movement of the threaded sleeve 20 can also be a composite shifting and rotational movement. The threaded sleeve 20 simply slaves the threaded rod 10 as far as it is shifted. Where the threaded sleeve 20 is rotated, the rotational movement of the threaded sleeve 20 generates an advancing movement of the threaded rod 10 relative to the threaded sleeve 20 via the second spindle drive formed by the threads 10a and 20i, as a result of a rotational block 40 on the threaded rod 10. In some embodiments, the spindle drives of the two shifting stages 10 and 20 are preferably each in the same direction.

FIG. 1 shows the drive device in a starting position. In the starting position, the overlapping shifting stages 10 and 20 are accommodated in a hollow space of the base part 1 and the drive 30. The shifting stages 10 and 20 are retracted up to a stopper, such that they maximally overlap.

Figure 2:
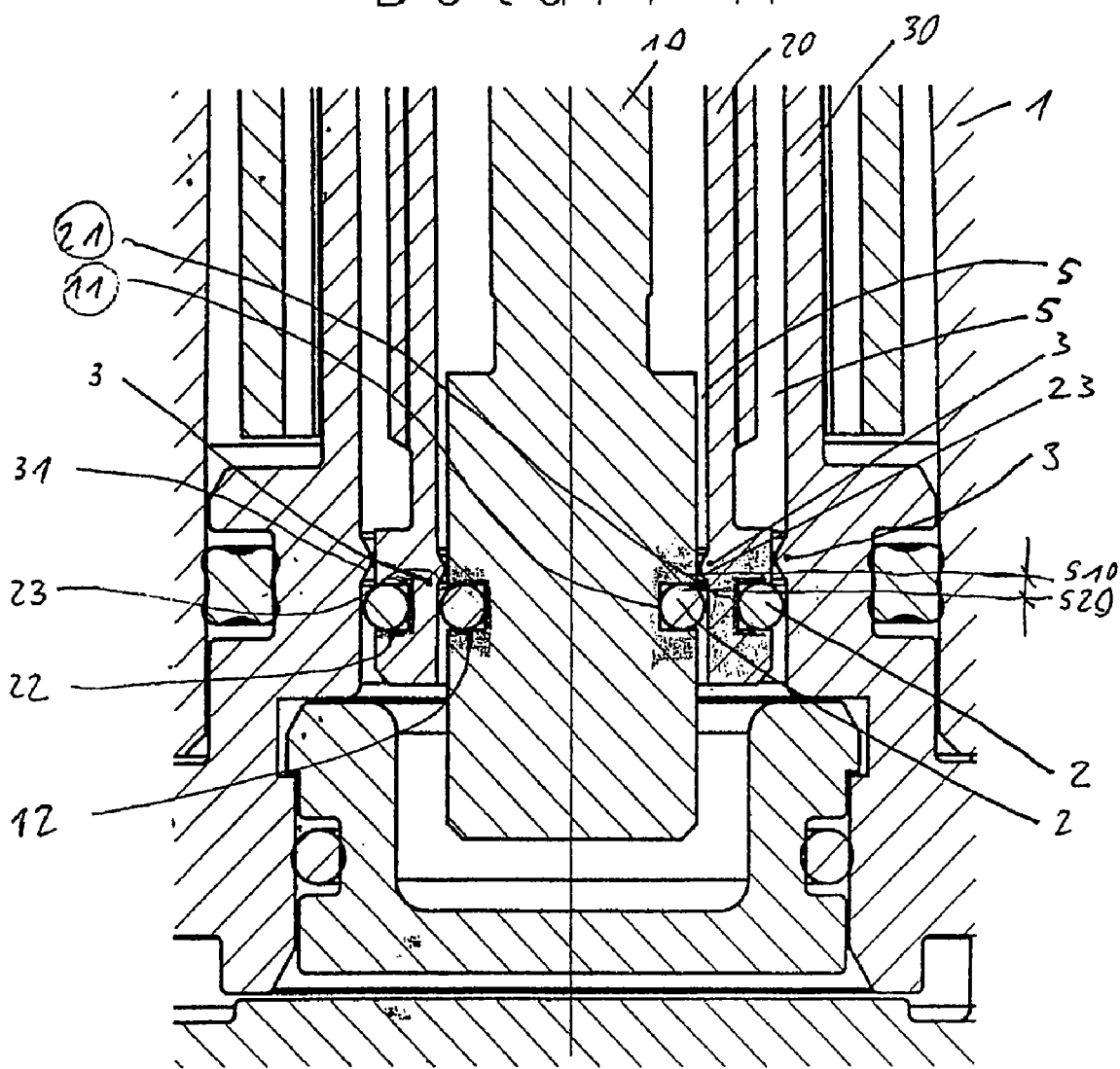
FIG. 2 is a more detailed view of area "R" from FIG. 1, depicting O-rings as resistance elements.

FIG. 2 shows a detail of the drive device. An O-ring 2 is accommodated in an annular groove 11 in the foot region of the first shifting stage 10. The O-ring 2 can be a conventional sealing ring. A further O-ring 2 is accommodated in an outer annular groove 21 of the second shifting stage 20. An axially extending intermediate space 5 is formed between the shifting stages 10, 20 and between the shifting stage 20 and the drive 30; each of the O-rings 2 or another flexible element can be shifted, substantially freely, in said intermediate space 5.

The O-rings 2 are pressed together in constrictions 3 in the intermediate space 5. The O-rings 2 form bearings for the shifting stages. The respective spindle drives form the second bearings. Each of the O-rings 2 is a flexible element which is pressed by the respective shifting stage in the advancing direction, against a corresponding radial protrusion 3. The protrusions 3 protrude perpendicular to the advancing direction of the shifting stages 10, 20, into the respective shifting path of the O-rings. A radial protrusion 3 is formed circumferentially on an inner surface area of the second shifting stage 20. Another radial protrusion 3 is circumferentially formed on an inner surface area of the drive 30. In the starting position of the drive device, the O-rings are each situated a pre-set shifting path length S10 or S20 in front of the radial protrusions 3 facing opposite them. The pre-set shifting path lengths S10, S20 can be the same. The shifting path lengths are pre-set by the position of the annular grooves 11 and 21.

If the O-rings 2 are held in their receptacles 11, 21 with play, this play can be added to the shifting path lengths.

In one embodiment, a resistance area 12 is formed by a rear limiting area of the groove 11. When the first shifting stage 10 is advanced relative to the second shifting stage 20, the resistance area 12 presses, indirectly via the O-ring, against a resistance counter area 23. The resistance counter area 23 is provided on the inner surface area of the second shifting stage 20. It is formed by the protrusion 3. When the first shifting stage 10 is advanced relative to the second shifting stage 20, the O-ring 2 between the resistance area 12 and the resistance counter area 23 is pressed together.

Correspondingly, a rear limiting area of the groove 21 forms a resistance area 22. The resistance area 22 presses via the other O-ring 2 onto a resistance counter area 31 formed by the protrusion 3 of the drive 30, and thus in the same way generates a higher resistance before passing the constriction.

Proceeding from the starting position described above, a first delivery takes place. Depending on the frictional conditions of the shifting stages 10 and 20, which follow from the internal friction of the spindle drives and the friction of the shifting stage bearings, either there is a relative movement in the first spindle drive, comprising threads 20a, 30i, such that the second shifting stage 20 is advanced first, or there is a relative movement in the second spindle drive, comprising threads 10a, 20i, such that the first shifting stage 10 is advanced first, relative to the base part and the second shifting stage. The shifting stage to which a lesser resistance against advancing is offered begins a shifting movement or is advanced more quickly. At the beginning of the relative movement in the corresponding spindle drive, the thread play of the spindle drive in the advancing direction is first compensated for, and then the shifting stage is advanced.

The respective pre-set shifting path length S10 or S20, by which a shifting stage is advanced before it experiences a higher resistance, at least in sections, against shifting further than does the other shifting stage, can be different for each shifting stage. The pre-set shifting path lengths S10, S20 are preferably selected so as to be as small as possible. They do not have to be adjusted to the play of the spindle drive. Preferably, they are adjusted to the distance by which the piston is advanced when primed. A sum of the pre-set shifting path lengths S10, S20 should be at most as large as the shifting path of the piston when the device is primed. Since each of the shifting stages 10, 20 is braked, at least in sections or at intervals, in accordance with the shifting path length S10, S20 set for it, which of the two shifting stages 10, 20 is advanced first is irrelevant for compensating for the play in the two spindle drives.

Figure 3:
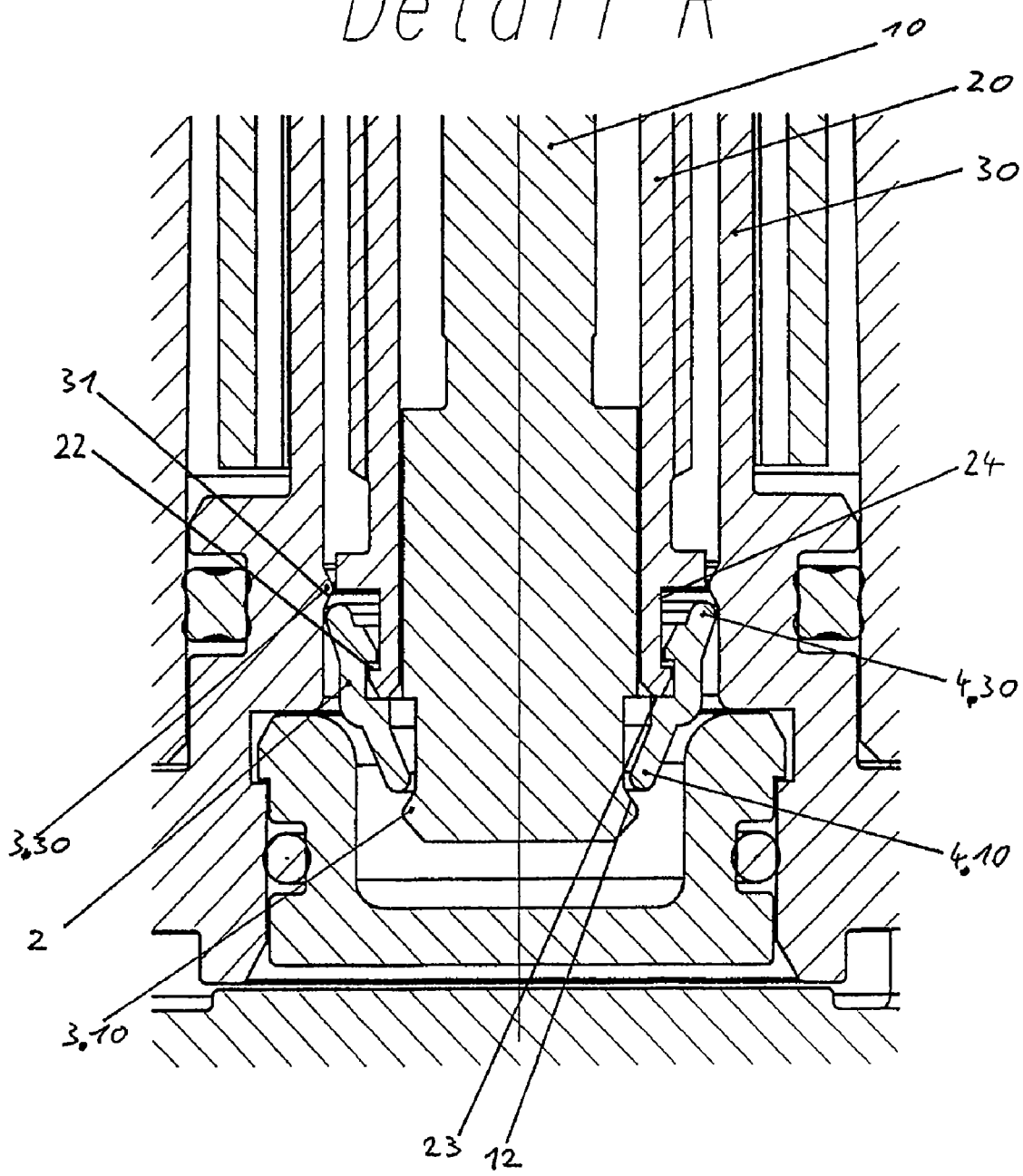
FIG. 3 is a more detailed view of area "R" an infusion device derived from FIG. 1, depicting a single resistance element in the form of an elastically flexible clip.

FIG. 3 shows a drive device in accordance with FIG. 1, with the difference that a common flexible element 2 is used for the two shifting stages 10, 20. The flexible element 2 is held in an annular groove 24 running around an outer surface area of the second shifting stage 20. The flexible element 2 is embodied as a rotating body made of a flexible material, preferably plastic. It comprises two elastically, flexibly moving clips 4.10, 4.30. A first clip 4.10 projects towards the first shifting stage 10, while the second clip 4.30 projects towards the drive 30 on the other side. At the rear end of the first shifting stage 10, a radial bulged protrusion 3.10 is formed which presses against the clip 4.10 of the flexible element 2 when the shifting stage 10 is shifted in the advancing direction relative to the shifting stage 20. When the second shifting stage 20 is advanced relative to the drive 30, the clip 4.30 is pressed against a radial bulge 3.30 of the drive 30. As in the previously described embodiment, a resistance area 12 or 22 presses first onto a resistance counter area 23 or 31 via a flexible resistance element 4.10 or 4.30. The resistance counter area 23 for the resistance area 12 is formed by a rear facing area of the second shifting stage 20. As in the previously described embodiment, the play in both spindle drives is compensated for at the beginning of the advancing movements of the two shifting stages 10, 20.

Figure 4:
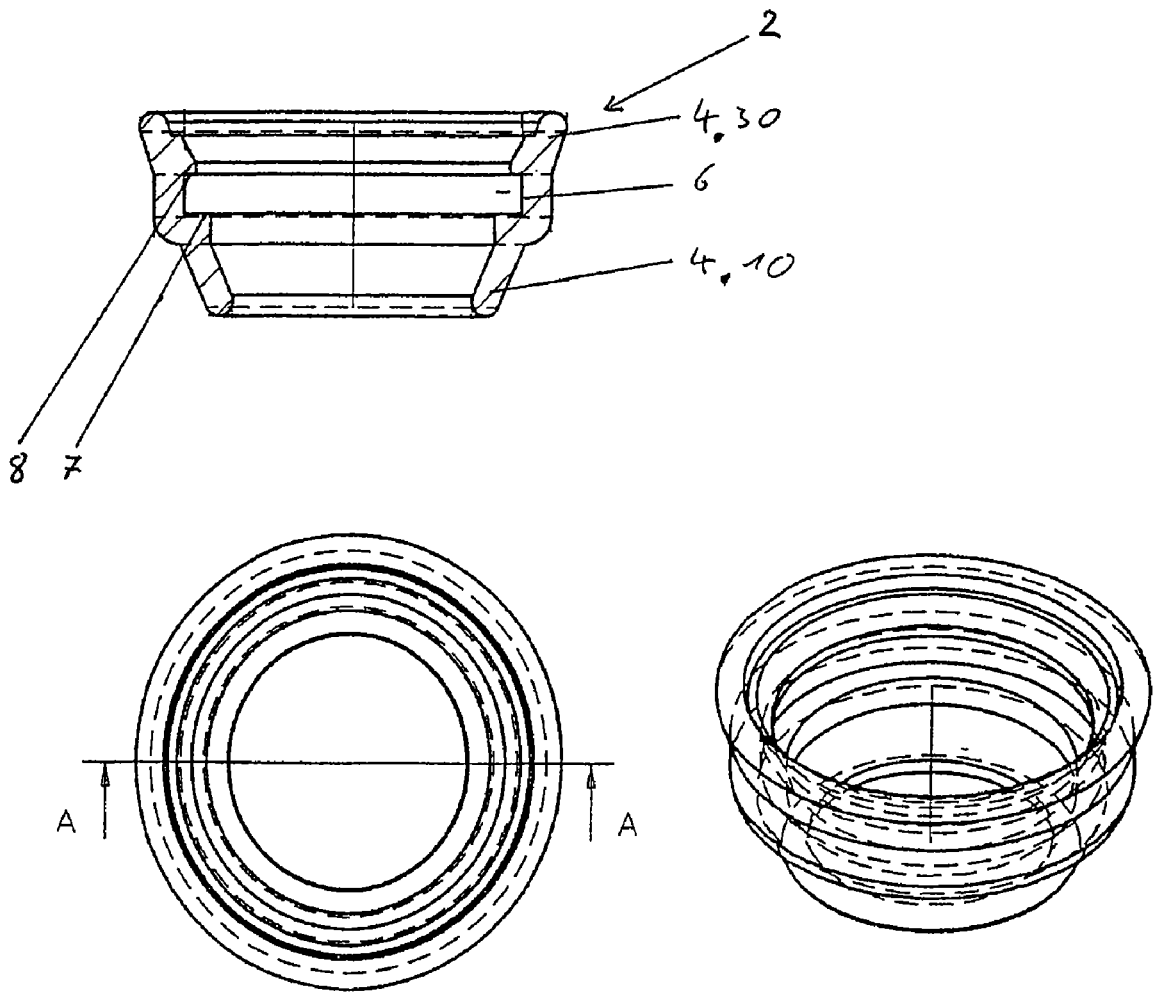
FIG. 4 depicts the resistance element of FIG. 3.

FIG. 4 shows the common flexible element 2 in accordance with FIG. 3, individually. The element preferably consists of one part. It could, however, also be composed of a number of components. The clips 4.10, 4.30 are closed in a circle. In order to brake the shifting stages, the clip 4.10 is pressed radially outwards and the clip 4.30 radially inwards. It is also possible to provide the resistance element or just the clips 4.10 and/or 4.30 with longitudinal slits or axial recesses. The flexible element 2 comprises a groove-shaped recess 6 on its inner surface area. A rear rim area 7 of this recess 6 is pressed against the resistance counter area 23 when the shifting stage 10 is first advanced relative to the shifting stage 20. A front rim area 8 serves to position the resistance area 22 against the flexible element 2.

Figure 5:
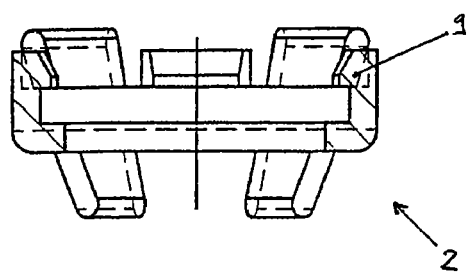
FIG. 5 depicts a modification of the resistance element of FIGS. 3 and 4.
Figure 5:
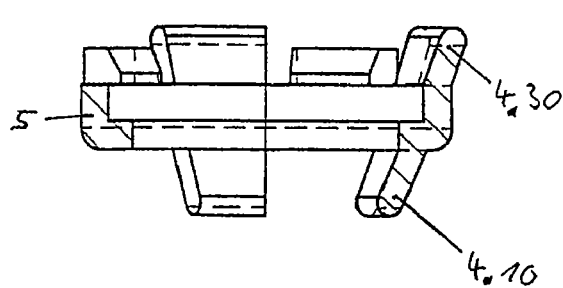
Figure 5:
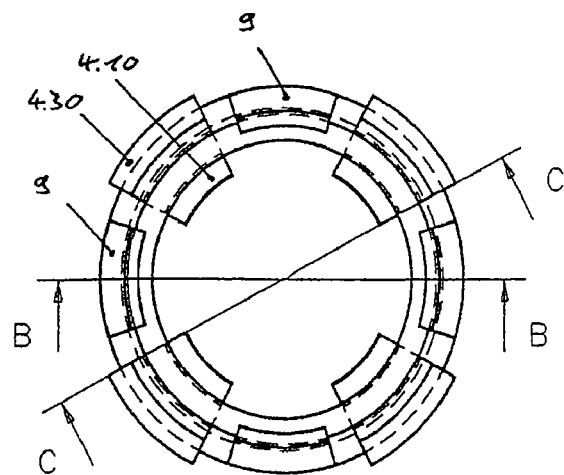
Figure 5:
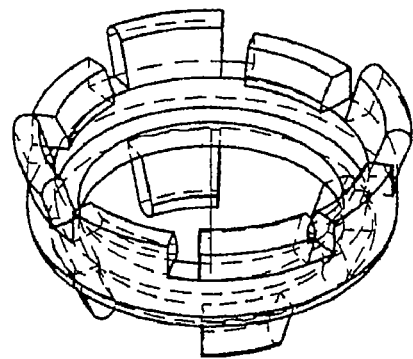

One example, in which the clips 4.10, 4.30 are only formed at individual segments of the circumference, may be seen in FIG. 5. The clips 4.10, 4.30 do not extend around the entire circumference. A center part 5 is given an annular form and connects the clips 4.30 to the clips 4.10. In the example depicts, four clips 4.10 and four clips 4.30 are each arranged evenly distributed around the circumference. Attaching hooks 9, likewise evenly distributed over the circumference, are provided, via which the flexible resistance element is axially attached in the annular groove 24 of the second shifting stage 20. They are arranged laterally offset with respect to the clips 4. This improves a slight mobility of the clips 4 in the radial direction. The increased resistance offered to a shifting stage when a radial protrusion presses against the clips 4.10, 4.30 in the axial direction is determined by the elasticity of the clips. This is dependent on the material used for the clips and on the shape of the clips. If a larger circumferential region is covered, then the force required to eject the clips increases generally.

In the foregoing description, embodiments of the invention, including preferred embodiments, have been presented for the purpose of illustration and description. They are not intended to be exhaustive or to limit the invention to the precise form disclosed. Modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A drive device for a piston in a container containing an injectable product, said drive device comprising:
   a) a first shifting stage which may be shifted relative to a base part from a starting position and which, when shifted in an advancing direction, advances said piston in said container, displacing product from said container in doses;
   b) at least a second shifting stage which may be shifted in said advancing direction relative to said base part from a starting position and which, when shifted in said advancing direction, slaves said first shifting stage;
   c) wherein said first shifting stage may be shifted in said advancing direction relative to said second shifting stage, and said first shifting stage and said second shifting stage at least partially overlap, viewed in said advancing direction;
   d) and a drive for advancing said shifting stages;
   e) wherein said drive acts on one of said shifting stages via a first spindle drive;
   f) and wherein a second spindle drive is formed between said shifting stages; wherein:
   g) proceeding from said starting position of said shifting stages, said shifting stage which is first advanced by a pre-set shifting path length experiences a higher resistance, at least in sections, against possibly shifting even further than does the other of the shifting stages, such that said other shifting stage is likewise advanced, wherein said higher resistance is can be overcome by the drive device such that said shifting stage that is first advanced is advanced further in the advancing direction after overcoming the higher resistance.

2. The drive device as set forth in claim 1, wherein said higher resistance is generated by a flexible resistance element against which said shifting stage which is advanced first presses once it has covered said pre-set path length.

3. The drive device as set forth in claim 2, wherein said resistance element is elastically flexible.

4. The drive device as set forth in claim 2, wherein said resistance element is formed by an O-ring.

5. The drive device as set forth in claim 2, wherein said resistance element is formed by a flexibly moving clip.

6. The drive device as set forth in claim 2, wherein each of said shifting stages, once it has been advanced by said respective path length, is pressed against a flexible resistance element when advanced further.

7. The drive device as set forth in claim 6, wherein a common flexible resistance element is provided for said shifting stages.

8. The drive device as set forth in claim 1, wherein:
   a resistance area is formed on a surface area of said first shifting stage;
   a resistance counter area is formed on a surface area with respect to which said first shifting stage may be shifted in said advancing direction; and
   said higher resistance is generated by a pressure exerted onto said resistance counter area by said resistance area.

9. The drive device as set forth in claim 8, wherein a flexible resistance element is arranged between said resistance area and said resistance counter area.

10. The drive device as set forth in claim 8, wherein said resistance area is formed by a collar and said resistance counter area is formed by a counter collar facing said collar.

11. The drive device as set forth in claim 1, wherein:
a resistance area is formed on a surface area of said second shifting stage;
a resistance counter area is formed on a surface area with respect to which said second shifting stage may be shifted in said advancing direction;
and said higher resistance is generated by a pressure exerted onto said resistance counter area by said resistance area.

12. The drive device as set forth in claim 11, wherein a flexible resistance element is arranged between said resistance area and said resistance counter area.

13. The drive device as set forth in claim 11, wherein said resistance area is formed by a collar and said resistance counter area is formed by a counter collar facing said collar.

14. The drive device as set forth in claim 1, wherein said spindle drives are provided with frictional resistances of different magnitudes.

15. The drive device as set forth in claim 1, wherein said pre-set shifting path length is shorter than a distance by which the piston is advanced during a priming movement.

16. A drive arrangement for an injection device, including a first stage, a second stage and a drive for shifting the stages, wherein the drive acts on one of the stages to shift said one of the stages first, wherein the stage which is shifted first encounters a higher resistance than does the other stage, such that the other stage is shifted, and wherein said higher resistance is overcome by the drive such that said shifting stage that is first shifted is shifted further after overcoming the higher resistance.

17. The drive arrangement according to claim 16, wherein the stages at least partially overlap and the first stage may be shifted relative to the second stage.

18. The drive arrangement according to claim 16, wherein the drive acts on said one of the stages via a first spindle drive and wherein a second spindle drive is formed between the stages.

* * * * *

UNITED STATES PATENT AND TRADEMARK OFFICE
CERTIFICATE OF CORRECTION

| | | |
|---|---|---|
| PATENT NO. | : 7,862,544 B2 | Page 1 of 1 |
| APPLICATION NO. | : 11/755439 | |
| DATED | : January 4, 2011 | |
| INVENTOR(S) | : Daniel Peter, Beat Spoerri and Hanspeter Niklaus | |

It is certified that error appears in the above-identified patent and that said Letters Patent is hereby corrected as shown below:

Col. 8, Line 35, "resistance is can be overcome" should read as -- resistance is overcome --

Signed and Sealed this
Twenty-third Day of August, 2011

David J. Kappos
*Director of the United States Patent and Trademark Office*